United States Patent
Green et al.

(10) Patent No.: US 11,564,868 B2
(45) Date of Patent: Jan. 31, 2023

(54) AUTOMATED MEDICATION DISPOSAL MESSAGING SYSTEM

(71) Applicant: MarkeTouch Media, Inc., Houston, TX (US)

(72) Inventors: Lyle M. Green, Pacific Palisades, CA (US); Charles E. Russo, Houston, TX (US); Matthew K. Feltman, Isle Of Palms, SC (US)

(73) Assignee: MarkeTouch Media, LLC, Houston, TX (US)

( * ) Notice: Subject to any disclaimer, the term of this patent is extended or adjusted under 35 U.S.C. 154(b) by 413 days.

(21) Appl. No.: 16/903,346

(22) Filed: Jun. 16, 2020

(65) Prior Publication Data

US 2021/0386629 A1 Dec. 16, 2021

(51) Int. Cl.
*A61J 7/04* (2006.01)
*G16H 20/10* (2018.01)
*G16H 40/67* (2018.01)

(52) U.S. Cl.
CPC ............ *A61J 7/0409* (2013.01); *G16H 20/10* (2018.01); *G16H 40/67* (2018.01); *A61J 2200/30* (2013.01)

(58) Field of Classification Search
CPC .... A61J 7/0409; A61J 2200/30; G16H 40/67; G16H 20/10
See application file for complete search history.

(56) References Cited

U.S. PATENT DOCUMENTS

| | | | |
|---|---|---|---|
| 5,431,299 A * | 7/1995 | Brewer | G07F 11/58 221/12 |
| 8,195,328 B2 * | 6/2012 | Mallett | G16H 40/67 221/102 |
| 8,204,620 B2 * | 6/2012 | Mallett | A61B 50/13 700/242 |
| 2007/0027432 A1 * | 2/2007 | Radford | F16K 5/0668 604/317 |
| 2008/0195247 A1 * | 8/2008 | Mallett | G07F 11/62 700/231 |
| 2013/0197927 A1 * | 8/2013 | Vanderveen | G06Q 10/10 705/2 |
| 2015/0148943 A1 * | 5/2015 | Sullivan | A61J 7/0076 700/231 |
| 2018/0113995 A1 * | 4/2018 | Hall | G06F 21/31 |

* cited by examiner

*Primary Examiner* — Michael Collins
(74) *Attorney, Agent, or Firm* — Brownstein Hyatt Farber Schreck, LLP (57) ABSTRACT

Techniques are described for automated medication disposal messaging. One method includes receiving information associated with a prescription order of a user account. In some cases, the information associated with the prescription order includes a medication identifier, medication dosage indication, and medication quantity. The method may include calculating a run out date corresponding to the target medication with the disposal guideline based on the medication dosage indication and the medication quantity. The method may also include communicating a disposal notification for the target medication based on the run out date.

20 Claims, 6 Drawing Sheets

AUTOMATED MEDICATION DISPOSAL MESSAGING SYSTEM

FIELD OF TECHNOLOGY

The present disclosure relates generally to database systems and data processing, and more specifically to automated medication disposal messaging system.

DESCRIPTION OF RELATED ART

A customer may engage a pharmacy to supply medicaments. Information regarding how to administer or consume the medicaments may be provided to the consumer. In some instances, specific or unique disposal guidelines of certain medicaments may exist. These disposal guidelines may not be known and/or understood by the consumer. Additionally, a pharmacy's post-sale contacts and/or processes associated with further communicating with the customer may be lacking. To support a pharmacy and other company's interactions with its customers, systems have been developed as a centralized, scalable mechanism related to various customer contact contexts, including, for example, sales and marketing contacts, service order contacts, technical support issues, and billing questions. A cloud platform (i.e., a computing platform for cloud computing) or hosted platform (i.e., a privately-managed computing platform utilizing cloud computing) may be employed by various entities to store, manage, and process data using a network of remote servers to support these systems.

SUMMARY

The described features generally relate to one or more improved methods, systems, or devices that provide techniques for providing automated medication disposal messaging. An example method may include receiving information associated with a prescription order of a user account. In some cases, the information associated with the prescription order may include a medication identifier, medication dosage indication, and medication quantity. The method may also include determining that the prescription order includes a target medication with an established disposal guideline based on the medication identifier. The method may also include calculating a run out date corresponding to the target medication with the disposal guideline based on the medication dosage indication and the medication quantity. Additionally, the method may include communicating a disposal notification for the target medication based on the run out date.

Apparatus for automated medication disposal messaging is described. An apparatus may include a processor, memory coupled with the processor, and instructions stored in the memory. The instructions may be executable by the processor to cause the apparatus to perform one or more of the operations described in the methods described herein.

Other apparatus for automated medication disposal messaging is described. An apparatus may include means for performing one or more of the operations described in the methods described herein.

Non-transitory computer-readable medium storing code for automated medication disposal messaging is described. Code may include instructions executable by a processor to perform one or more of the operations described in the methods described herein.

DETAILED DESCRIPTION

In accordance with some aspects of the present disclosure, a server may receive information associated with the prescription order of a user account. In some cases, the information associated with the prescription order includes a medication identifier, medication dosage indication, and medication quantity. In some examples, the medication identifier may be a drug name, a generic code number, a national drug code, or a generic product identifier. The medication identifier may be used by the server to determine that the prescription order includes a target medication with specified disposal guidelines. In some cases, the target medication may be designated as a controlled substance (e.g., as designated by the United States Drug Enforcement Agency (DEA)), and therefore may have particular disposal guidelines. In some cases, the target medication may be designated as a medication with disposal recommendations issued by a government agency (e.g., the United States Food & Drug Administration (FDA) or the United States Environmental Protection Agency (EPA)). In some examples, the medication dosage indication may be a daily medication dosage or a total days' supply dispensed. In some examples, the medication quantity comprises a total quantity of medication dispensed. One or both of the medication dosage indication or the medication quantity may be used by the server to calculate a run out date of the target medication. That is, the server may determine that the prescription order includes the target medication with a disposal guideline based at least in part on the medication identifier and calculate the run out date corresponding to the target medication with the disposal guideline based at least in part on the medication dosage indication and/or the medication quantity. In some examples, the run out date refers to the date at which a patient would exhaust the dispensed supply of medication, if taken as prescribed. The server may communicate a disposal notification for the target medication using various techniques.

For example, the timing of the communicating the disposal notification for the target medication by the server may be based at least in part on run out date. In some cases, the server may communicate the disposal notification for the target medication on the run out date. In some cases, the server may communicate the disposal notification for the target medication on a date that is less than a determined number of days before or after the run out date, for example if the run out date is on a weekend or holiday, or one or more reminders proximal to the run-out date is desirable. The determined number of days may be based on the overall number of days for consumption of the target medication (e.g., a fewer determined number of days for a prescription order that is a week's supply of the target medication as compared to a month's supply of the target medication). The server may also determine for how to communicate the disposal notification for the target medication based on the received information associated with the prescription. That is, the information associated with the prescription may include information for providing contact associated with the user account. For example, the information for providing contact associated with the user account may include at least one of a primary contact number or a patient identifier. The disposal notification for the target medication communicated by the server may include disposal instructions for any remaining target medication associated with the prescription order. For example, the disposal instructions may include instructions to utilize a neutralizing compound on any remaining target medication associated with the prescription order. In some cases, the neutralizing compound may have already been provided in conjunction with the prescription order. In other examples, the disposal instructions may include instructions to return any remaining medication associated with the prescription order to a designated location. The designation location may be associated with a take-back locker or kiosk in a facility (e.g., a facility of the pharmacy that completed the prescription order.) In some cases, the designation location may be associated with a law enforcement facility (e.g., a local law enforcement facility or location be available to take back and properly dispose controlled substances).

In some examples, the server may identify a text-capable contact number associated with the information associated with the prescription order and transmit a message (e.g., SMS/MMS text message) via the text-capable contact number to communicate the disposal notification for the target medication based at least in part on the run out date. In some examples, the server may identify that a device associated with the user account comprises an application. For example, the device associated with the user account may include an iOS or Android-based application thereby enabling the device to operate as a client of the server, or otherwise communicate with the server. The server may transmit a push notification or message via the device to communicate the disposal notification for the target medication based at least in part on the run out date. In some examples, the server may identify a contact number associated with the information for providing contact associated with the user account. The server may place an outbound call (to the contact number and provide an automated message (e.g., an Interactive Voice Response (IVR) audio message) to communicate the disposal notification for the target medication based at least in part on the run out date. In some examples, the server (or an IVR component associated therewith) may receive an incoming call from an inbound number. The server may identify the prescription order of the user account user based at least in part on the inbound number and the information associated with the prescription order. The server may provide an automated message (e.g., an IVR audio message) at some time during the inbound call to communicate the disposal notification for the target medication based at least in part on the run out date. In some examples, responsive to the communicating the disposal notification for the target medication, the server may receive a notification that all medication associated with the prescription order was consumed. In some examples, responsive to the communicating the disposal notification for the target medication, the server may receive a notification that any remaining medication associated with the prescription order was disposed. In some cases, the server may communicate the response notification from a patient or user of user account to a pharmacy or entity that provided the prescription order.

Inventive aspects of the subject technology provide one or more solutions to various problems associated dispensed, but unused medications. For example, an extensive number of excess doses of unused controlled substance and dangerous prescription medications reside in American households. According to one account, a majority of prescriptions for opioid tablets prescribed after surgery went unused and are potentially available for abuse. To assist in the safe removal of these medications, certain pharmacies have implemented various types of drug disposal processes or take back services. For example, a pharmacy location may include drug take-back receptacles. Additionally or alternatively, a drug disposal system may be provided with each dispensing of a controlled substance medication. Similarly, medications (whether or not classified as a controlled substance) may include specific FDA or EPA disposal recommendations. These medications may be hazardous to the environment and/or other persons if disposed in an improper manner (e.g., pouring the medication down a sink or flushing the medication down a toilet). That is, the target medications with disposal guidelines may include a group of medication where the FDA or EPA has determined that certain medications (e.g., hormones, cardiac medications, antibiotics, etc.) should be properly disposed to avoid entry into the water system.

Benefits of the inventive system for automated medication disposal messaging include, but are not limited to: (i) increasing patient awareness to appropriate drug disposal practices and services; (ii) providing an additional means to combat prescription drug abuse/addiction (e.g., curbing the opioid epidemic); (iii) ensuring medication disposal program message is delivered to a patient receiving a prescription to a target medication with disposal guidelines; and (iv) lowering the overall cost of healthcare through improved patient literacy and medication pricing.

Aspects of the disclosure are initially described in the context of an environment supporting a database. A server may access the database to provide medication disposal messaging. Aspects of the disclosure are further illustrated by and described with reference to apparatus diagrams, system diagrams, and flowcharts that relate to medication disposal messaging.

Figure 1:
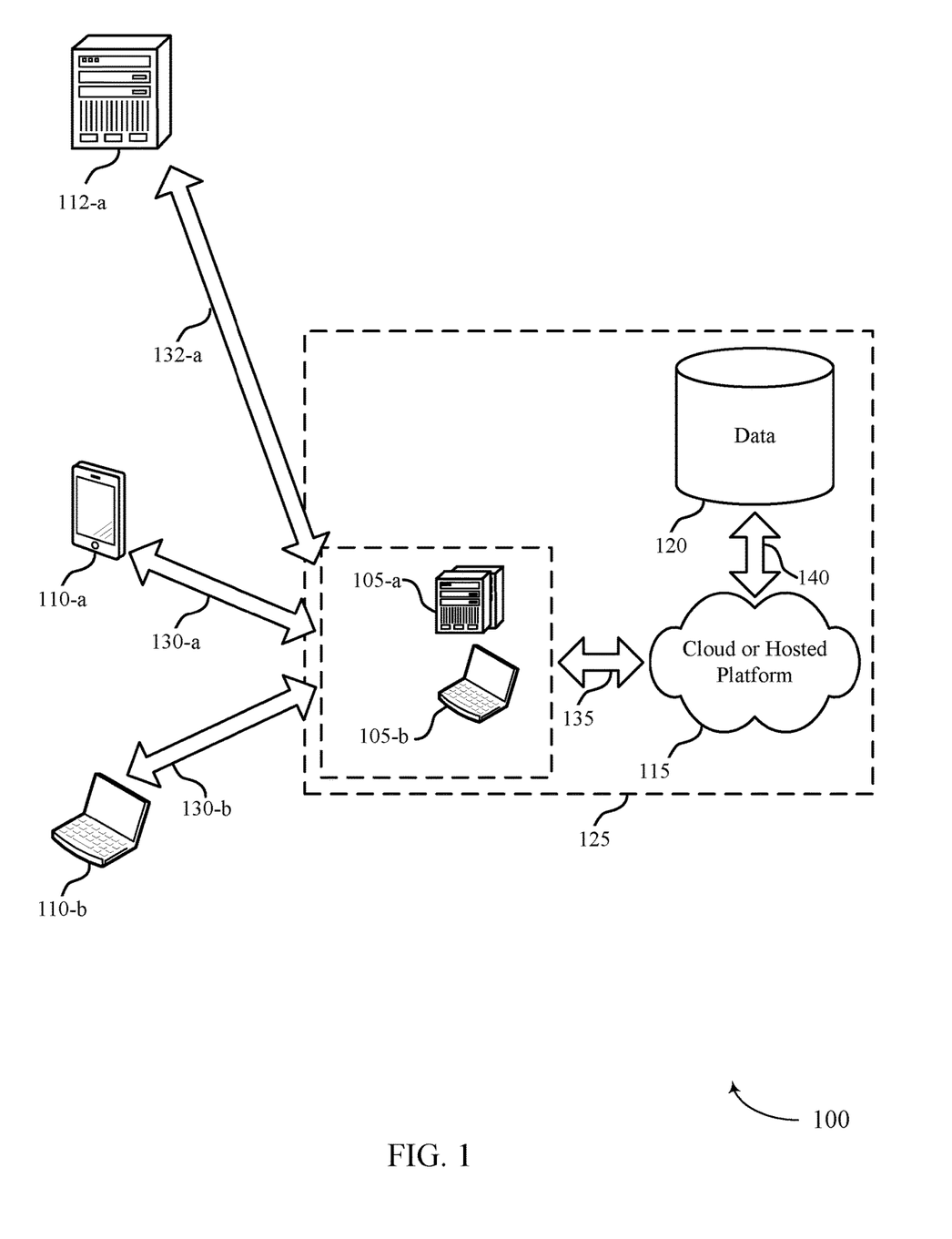
FIG. 1 illustrates an example of a system for medication disposal messaging that supports automated medication disposal messaging system in accordance with aspects of the present disclosure.

FIG. 1 illustrates an example of a system 100 for cloud computing that supports automated medication disposal messaging in accordance with various aspects of the present disclosure. The system 100 includes client 105 (e.g., a cloud client or hosted client), user device contacts 110, remote system contacts 112, cloud platform 115, and data access 120. Cloud platform 115 may be an example of a public or private cloud network. A client 105 may access cloud platform 115 over network connection 135. The network may implement transfer control protocol and internet protocol (TCP/IP), such as the Internet, or may implement other network protocols. A client 105 may be an example of a user device, such as a server (e.g., client 105-*a*) or a laptop (e.g., client 105-*b*). In other examples, a client 105 may be a desktop computer, a tablet, or another computing device or system capable of generating, analyzing, transmitting, or receiving communications. In some examples, a client 105 may be operated by a user entity that is part of a business or other organization type (e.g., an entity responsible for providing consumer contact).

A client 105 may interact with multiple user device contacts 110. The interactions 130 may include communications, opportunities, purchases, sales, or any other interaction between a client 105 and a user device contact 110. Data may be associated with the interactions 130. A client 105 may access cloud or hosted platform 115 to store, manage, and process the data associated with the interactions 130. In some cases, the client 105 may have an associated security or permission level. A client 105 may have access to certain applications, data, and database information within cloud or hosted platform 115 based on the associated security or permission level, and may not have access to others.

Client 105 may interact with user device contacts 110 via text messaging, email, voice call, or any other appropriate form of interaction (e.g., interactions 130-*a*, or 130-*b*). In some examples, the interaction 130 may be a business-to-consumer (B2C) interaction. A user device contact 110 may also be referred to as or associated with a consumer, a customer, or some other suitable terminology. In some cases, the user device contact 110 may be an example of a user device, such as a mobile device (e.g., user device contact 110-*a*) or a laptop (e.g., user device contact 110-*b*). In other cases, the user device contact 110 may be another computing device that a consumer may own capable of electronic communication. In some cases, the user device contact 110 may be operable by a consumer or user authorized to access a user account.

Client 105 may also interact with remote system contacts 112 via application programming interface (API), web communication, or any other appropriate form of interaction or computing interface (e.g., interactions 132-*a*). In some examples, the interaction 130 may be a business-to-business (B2B) interaction. A remote system contact 112 may also be referred to as a third-party system, third-party entity, or some other suitable terminology. In some cases, the remote system contacts 112 may be an example of a server at a location different from a location of client 105. In some cases, the remote system contact 112 may be operated by one or more users or an entity different from users or an entity associated with client 105. In other cases, the remote system contact 112 may be operated by the same users or entity as the those associated with client 105.

Cloud or hosted platform 115 may provide data access or database service for the client 105. In some cases, cloud or hosted platform 115 may be an example of a single-tenant or multi-tenant database system. However, other types of systems may be implemented, including—but not limited to—client-server systems, mobile device systems, and mobile network systems. In some cases, cloud or hosted platform 115 may support customer relationship management (CRM) solutions. In some examples, the CRM solutions may include support for consumer contact, order and service fulfillment, marketing, etc. Cloud or hosted platform 115 may receive data associated with contact interactions 130 from the client 105 over network connection 135. Cloud or hosted platform 115 may receive data associated with contact interactions 132 from the client 105 over network connection 135. In some cases, cloud or hosted platform 115 may receive data directly from an interaction 130 between a user device contact 110 and the client 105. In some cases, the user device contact 110 may run an application that includes communication with client 105 and/or cloud or hosted platform 115. Cloud or hosted platform 115 may be implemented using remote servers. In some cases, the remote servers may be located at one or more data centers 120.

Data center 120 may include multiple servers. The multiple servers may be used for data storage, management, and processing. Data center 120 may receive data from cloud platform 115 via connection 140, or directly from the cloud client 105 or an interaction 130 between a contact 110 and the cloud client 105. Data center 120 may utilize multiple redundancies for security purposes. In some cases, the data stored at data center 120 may be backed up by copies of the data at a different data center (not pictured).

Subsystem 125 may include cloud clients 105, cloud platform 115, and data center 120. In some cases, data processing may occur at any of the components of subsystem 125, or at a combination of these components. In some cases, servers may perform the data processing. The servers may be a cloud client 105 or located at data center 120.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

In accordance with some implementations, client 105 (e.g., one or more consumer preference and maintenance interface servers implementing automated medication disposal messaging techniques) may receive, from a remote system contact 112 (e.g., a pharmacy management software system), information associated with the prescription order of a user account, where the information associated with the prescription order includes a medication identifier, medication dosage indication, and medication quantity. Client 105 may determine that the prescription order includes a target medication with a disposal guideline based on the medication identifier. Client 105 calculate a run out date corresponding to the target medication with the disposal guideline based on the medication dosage indication and the medication quantity. Client 105 may communicate a disposal notification for the target medication based on the run out date.

Figure 2:
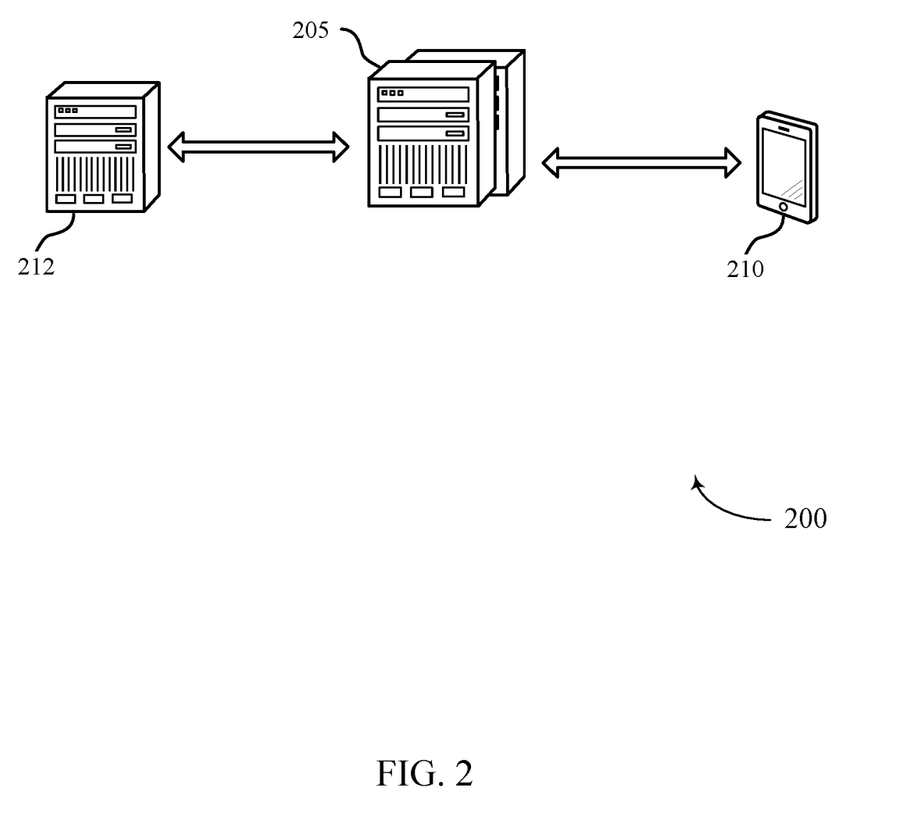
FIG. 2 illustrates an example of a system for medication disposal messaging that supports that supports automated medication disposal messaging in accordance with aspects of the present disclosure.

FIG. 2 illustrates an example of a client 205 (e.g., one or more consumer preference and maintenance interface servers) that supports automated medication disposal messaging in accordance with aspects of the present disclosure. A pharmacy management software system 212 may process prescription orders associated with user accounts. Client 205 may obtain prescription filling data files from the pharmacy management software system 212. In some cases, client 205 may obtain prescription filling data files from a third party server of system different from the pharmacy management software system 212 (e.g., a third party server or system that communicates or received files from the pharmacy management software system 212).

Client 205 may receive information from the prescription filling data files for a prescription order of a user account. This information associated with the prescription order may include a medication identifier. In some cases, the medication identifier may be a drug name, national drug code or generic product identifier. Client 205 may identify that the dispensed medication associated with the prescription order is a target medication based at least in part on the medication identifier. For example, client 205 may use the drug name, national drug code, or generic product identifier to identify that the dispensed medication is either a DEA designated controlled substance (e.g., a Schedule II-V controlled substance) or a medication with specific FDA or EPA disposal guidelines. Client 205 may thus designate the dispensed medication as a target medication with disposal guidelines. In accordance with some aspects, client 205 may utilize automated daily processes to ensure that the most up to date DEA scheduling as well as FDA and/or EPA guidance for medication disposal is accessed and can be provided to patients via the communicating the disposal notification.

Client 205 may identify the target medication for disposal messaging. The received information from the prescription filling data files for the prescription order of the user account may also include a medication dosage indication and medication quantity. For example, the medication dosage indication may include a daily medication dosage, a total days' supply dispensed, or the like. The medication quantity may include a total quantity of medication dispensed or the like. In some cases, the medication quantity may be based values or measurements in accordance with pills, powder, or liquid examples of a particular target medication. In some cases, the medication dosage indication and medication quantity can be determined from a single data element from the prescription filling data files for the particular prescription order of the user account. Client 205 may calculate a run out date using this information (e.g., a daily medication dosage, total days' supply dispensed, a total quantity of medication dispensed, etc.).

For example, client 205 may receive information associated with a prescription order of a user account indicating that a 7-day supply of Vicodin® was dispensed on Mar. 17, 2020 (day 1). Vicodin® is designated by the DEA as a Schedule II controlled substance and client 205 determines the Vicodin® dispensed from the prescription order associated with the user account to be a target medication with disposal guidelines. Client 205 may determine that 7-day supply of Vicodin® based on a daily medication dosage of three tablets per day (e.g., one tablet per mouth every 6 hours as needed) and a total for 21 tablets. Thus, client 205 may calculate the run out date to be Mar. 24, 2020 (day 8). That is, client 205 may determine the run out date to be the day when all tablets of the target medication (e.g., 7-day supply of Vicodin®) should have been consumed by a patient for whom the prescription order of the user account was intended. On Mar. 24, 2020 (day 8), client 205 will communicate a disposal notification (e.g., an appropriate disposal information message) based at least in part on the run out date. The disposal notification may be provided in accordance with a delivery preference (e.g., SMS/MMS text message, voice call, mobile device app push notification, etc.) of the user account. Information included in the disposal notification may include, but is not limited to, the proper disposal of the target medication or any products or services provided by a pharmacy partner for such disposal. For example, the disposal notification may include instruction for using a neutralizing compound (e.g., a powder or solution having the ability of neutralizing the target medication), or instructions for using other types of decontamination technologies for rendering the target medication with disposal guidelines insoluble. Additionally or alternatively, the disposal notification may include information concerning a disposal location such as, but not limited to, a take-back locker or kiosk in a pharmacy.

In accordance with some aspects, the disposal messaging system may communicate the disposal notification in accordance with a known preference for the user account. In some examples, client 205 transmit a message (e.g., SMS/MMS text message) via a text-capable contact number corresponding to user device contact 210 to communicate the disposal notification for the target medication. In some examples (e.g., when user device contact 210 includes has an application that includes communication with client 205), client 205 may transmit a push notification or message to user device contact 210 to communicate the disposal notification for the target medication. In some examples, client 205 may place an outbound call to a contact number for user device contact 210. Client 205 may provide an automated message (e.g., an IVR audio message) during the outbound call to communicate the disposal notification for the target medication. In some examples, client 205 may receive an inbound call from a contact number corresponding to user device contact 210. client may identify the prescription order of the user account user based at least in part on the contact number of the inbound call from the user device contact 210 and knowledge that the user device contact 210 is associated with the user account of a prescription order identified to include a target medication. Client 205 may provide an automated message (e.g., an IVR audio message) at some time during the inbound call to communicate the disposal notification for the target medication. For example, client 205 may determine that a run out date has passed with respect to the target medication and may determine based on a date of the inbound call being within a designated timeframe (e.g., within one week from the run out date) for providing a disposal notification (e.g., either an initial disposal notification or a subsequent disposal notification).

Responsive to the disposal notification, user device contact 210 may communicate a response notification to client 205 that all medication associated with the prescription order was consumed or that any remaining medication associated with the prescription order was disposed. In some cases, client 205 may communicate to the pharmacy management software system 212 that a disposal message was communicated to the user device contact 210. In some cases, client 205 may communicate the response notification (received from the user device contact 210) to the pharmacy management software system 212.

Figure 3:
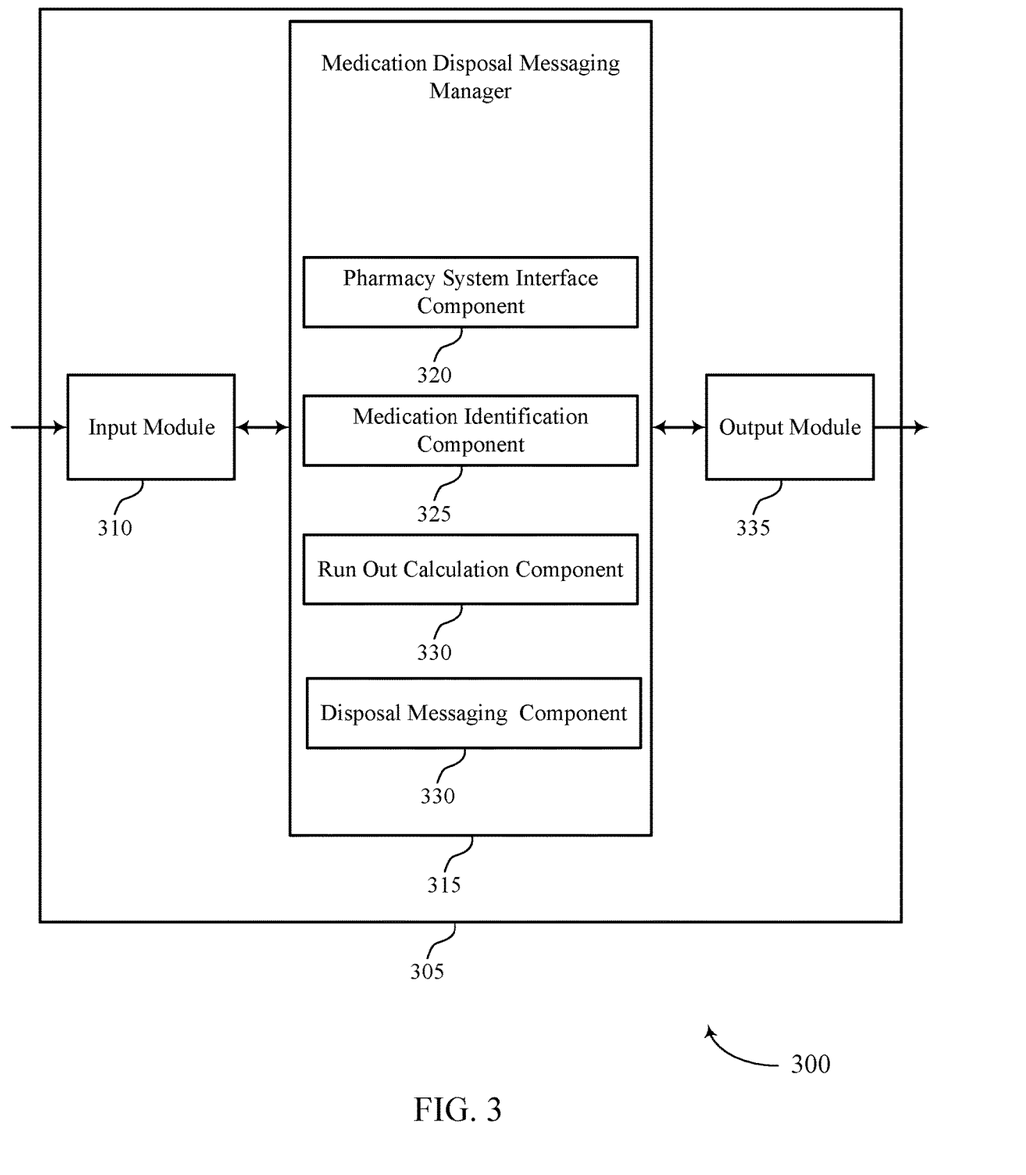
FIG. 3 shows a block diagram of an apparatus that supports automated medication disposal messaging system in accordance with aspects of the present disclosure.

FIG. 3 shows a block diagram 300 of an apparatus 305 that supports automated medication disposal messaging system in accordance with aspects of the present disclosure. The apparatus 305 may include an input module 310, a medication disposal messaging manager 315, and an output module 340. The apparatus 305 may also include a processor. Each of these components may be in communication with one another (e.g., via one or more buses). In some cases, the apparatus 305 may be an example of a user terminal, a database server, or a system containing multiple computing devices.

The input module 310 may manage input signals for the apparatus 305. For example, the input module 310 may identify input signals based on an interaction with a modem, a keyboard, a mouse, a touchscreen, or a similar device. These input signals may be associated with user input or processing at other components or devices. In some cases, the input module 610 may utilize an operating system such as iOS®, ANDROID®, MS-DOS®, MS-WINDOWS®, OS/2®, UNIX®, LINUX®, or another known operating system to handle input signals. The input module 310 may send aspects of these input signals to other components of the apparatus 305 for processing. For example, the input module 310 may transmit input signals to the medication disposal messaging manager 315 to support automated medication disposal messaging system. In some cases, the input module 310 may be a component of an input/output (I/O) controller 515 as described with reference to FIG. 5.

The medication disposal messaging manager 315 may include a pharmacy system interface component 320, a medication identification component 325, a run out calculation component 330, and a disposal messaging component 335. The medication disposal messaging manager 315 may be an example of aspects of the medication disposal messaging manager 405 or 510 described with reference to FIGS. 4 and 5.

The medication disposal messaging manager 315 and/or at least some of its various sub-components may be implemented in hardware, software executed by a processor, firmware, or any combination thereof. If implemented in software executed by a processor, the functions of the medication disposal messaging manager 315 and/or at least some of its various sub-components may be executed by a general-purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described in the present disclosure. The medication disposal messaging manager 315 and/or at least some of its various sub-components may be physically located at various positions, including being distributed such that portions of functions are implemented at different physical locations by one or more physical devices. In some examples, the medication disposal messaging manager 315 and/or at least some of its various sub-components may be a separate and distinct component in accordance with various aspects of the present disclosure. In other examples, the medication disposal messaging manager 315 and/or at least some of its various sub-components may be combined with one or more other hardware components, including but not limited to an I/O component, a transceiver, a network server, another computing device, one or more other components described in the present disclosure, or a combination thereof in accordance with various aspects of the present disclosure.

The pharmacy system interface component 320 may receive information associated with a prescription order of a user account, where the information associated with the prescription order includes a medication identifier, medication dosage indication, and medication quantity.

The medication identification component 325 may determine that the prescription order includes a target medication with a disposal guideline based on the medication identifier.

The run out calculation component 330 may calculate a run out date corresponding to the target medication with the disposal guideline based on the medication dosage indication and the medication quantity.

The disposal messaging component 335 may communicate a disposal notification for the target medication based on the run out date.

The output module 340 may manage output signals for the apparatus 305. For example, the output module 340 may receive signals from other components of the apparatus 305, such as the medication disposal messaging manager 315, and may transmit these signals to other components or devices. In some specific examples, the output module 340 may transmit output signals for display in a user interface, for storage in a database or data store, for further processing at a server or server cluster, or for any other processes at any number of devices or systems. In some cases, the output module 340 may be a component of an I/O controller 515 as described with reference to FIG. 5.

Figure 4:
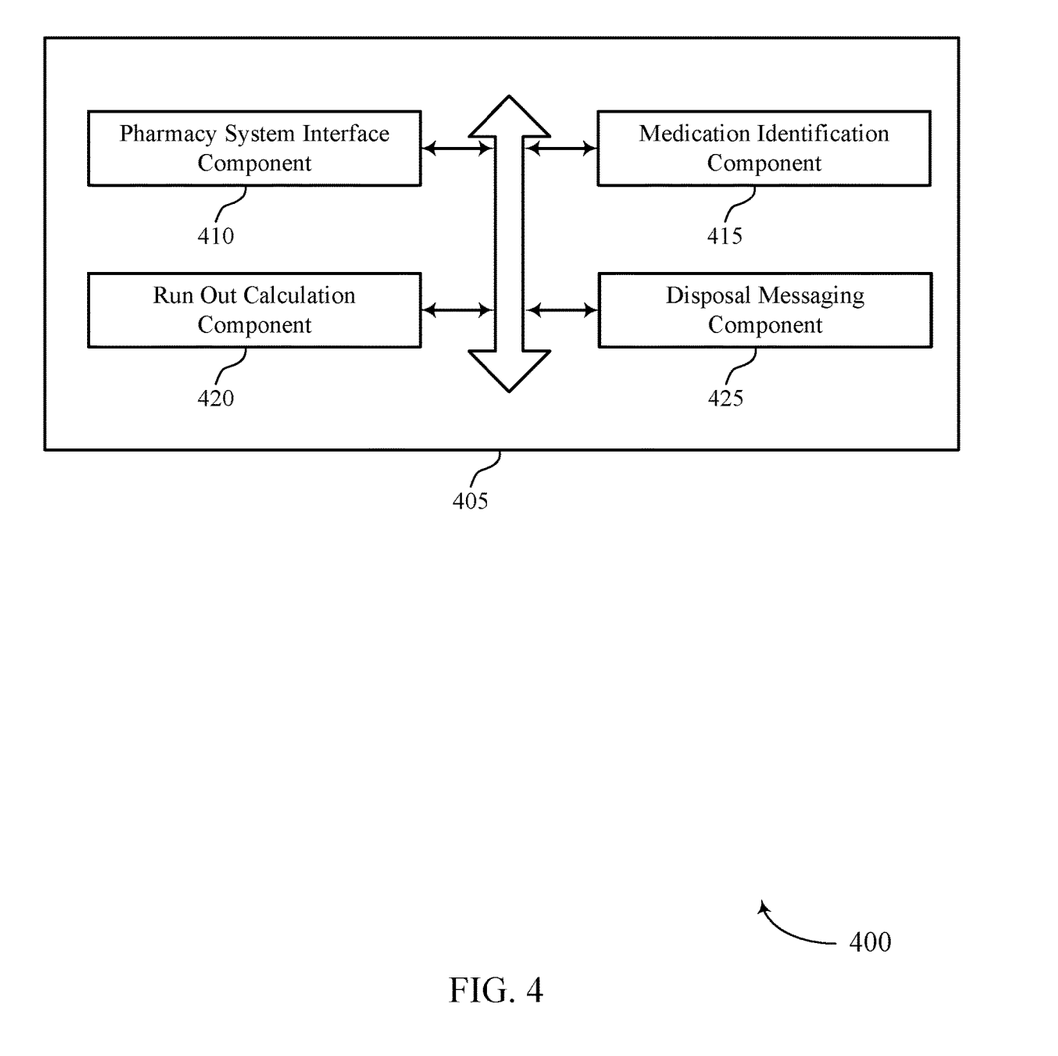
FIG. 4 shows a block diagram of a medication disposal messaging manager that supports automated medication disposal messaging system in accordance with aspects of the present disclosure.

FIG. 4 shows a block diagram 400 of a medication disposal messaging manager 405 that supports automated medication disposal messaging system in accordance with aspects of the present disclosure. The medication disposal messaging manager 405 may be an example of aspects of a medication disposal messaging manager 315 or a medication disposal messaging manager 510 described herein. The medication disposal messaging manager 405 may include a pharmacy system interface component 410, a medication identification component 415, a run out calculation component 420, and a disposal messaging component 425. Each of these modules may communicate, directly or indirectly, with one another (e.g., via one or more buses).

The pharmacy system interface component 410 may receive information associated with a prescription order of a user account, where the information associated with the prescription order includes a medication identifier, medication dosage indication, and medication quantity.

The medication identification component 415 may determine that the prescription order includes a target medication with a disposal guideline based on the medication identifier.

The run out calculation component 420 may calculate a run out date corresponding to the target medication with the disposal guideline based on the medication dosage indication and the medication quantity.

The disposal messaging component 425 may communicate a disposal notification for the target medication based on the run out date.

Figure 5:
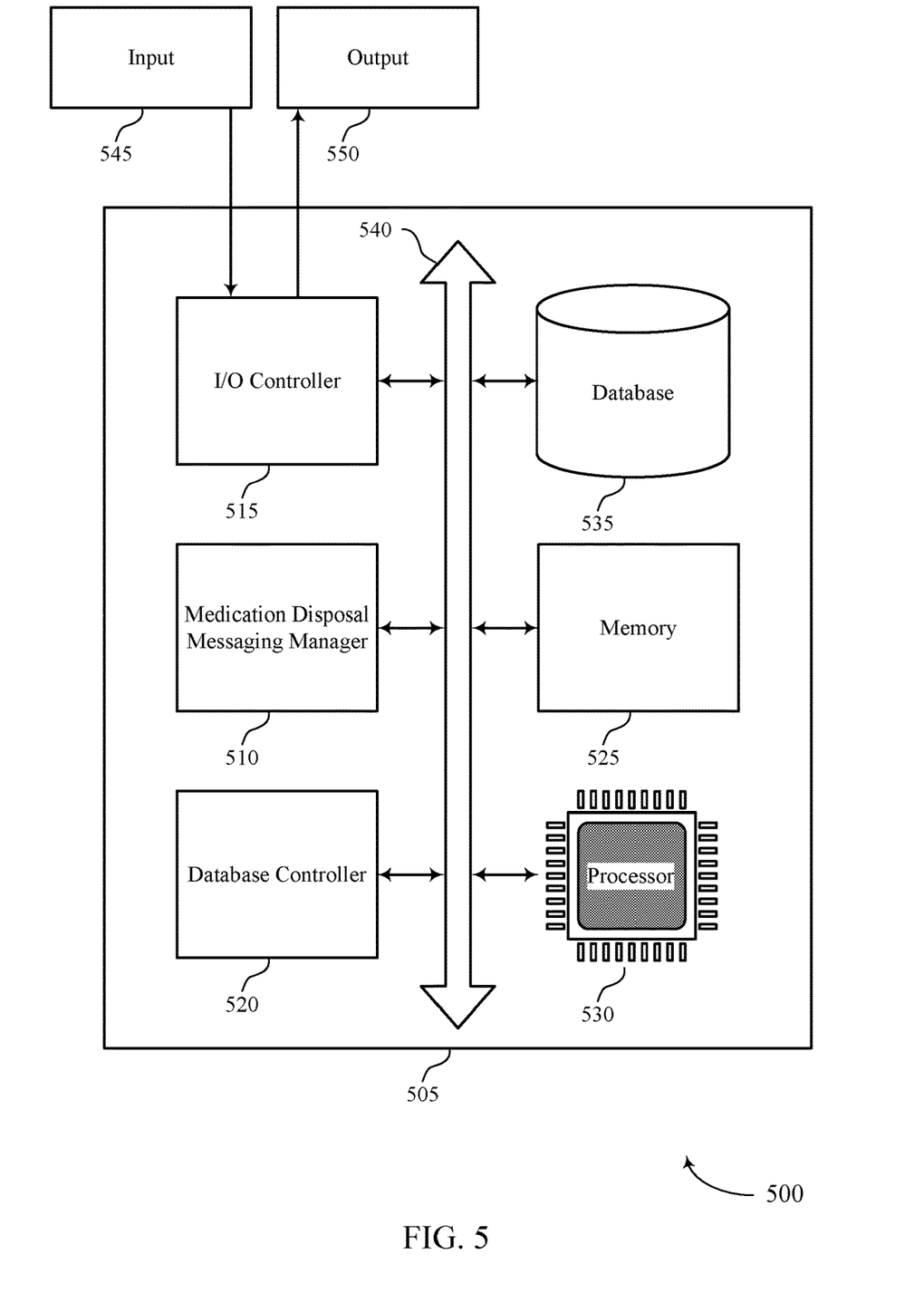
FIG. 5 shows a diagram of a system including a device that supports automated medication disposal messaging system in accordance with aspects of the present disclosure.

FIG. 5 shows a diagram of a system 500 including a device 505 that supports automated medication disposal messaging system in accordance with aspects of the present disclosure. The device 505 may be an example of or include the components of a database server or an apparatus 305 as described herein. The device 505 may include components for bi-directional data communications including components for transmitting and receiving communications, including a medication disposal messaging manager 510, an I/O controller 515, a database controller 520, memory 525, a processor 530, and a database 535. These components may be in electronic communication via one or more buses (e.g., bus 540).

The medication disposal messaging manager 510 may be an example of a medication disposal messaging manager 315 or 405 as described herein. For example, the medication disposal messaging manager 510 may perform any of the methods or processes described above with reference to FIGS. 3 and 4. In some cases, the medication disposal messaging manager 510 may be implemented in hardware, software executed by a processor, firmware, or any combination thereof.

The I/O controller 515 may manage input signals 545 and output signals 550 for the device 505. The I/O controller 515 may also manage peripherals not integrated into the device 505. In some cases, the I/O controller 515 may represent a physical connection or port to an external peripheral. In some cases, the I/O controller 515 may utilize an operating system such as iOS®, ANDROID®, MS-DOS®, MS-WINDOWS®, OS/2®, UNIX®, LINUX®, or another known operating system. In other cases, the I/O controller 515 may represent or interact with a modem, a keyboard, a mouse, a touchscreen, or a similar device. In some cases, the I/O controller 515 may be implemented as part of a processor. In some cases, a user may interact with the device 505 via the I/O controller 515 or via hardware components controlled by the I/O controller 515.

The database controller 520 may manage data storage and processing in a database 535. In some cases, a user may interact with the database controller 520. In other cases, the database controller 520 may operate automatically without user interaction. The database 535 may be an example of a single database, a distributed database, multiple distributed databases, a data store, a data lake, or an emergency backup database.

Memory 525 may include random-access memory (RAM) and read-only memory (ROM). The memory 525 may store computer-readable, computer-executable software including instructions that, when executed, cause the processor to perform various functions described herein. In some cases, the memory 525 may contain, among other things, a basic input/output system (BIOS) which may control basic hardware or software operation such as the interaction with peripheral components or devices.

The processor 530 may include an intelligent hardware device, (e.g., a general-purpose processor, a DSP, a central processing unit (CPU), a microcontroller, an ASIC, an FPGA, a programmable logic device, a discrete gate or transistor logic component, a discrete hardware component, or any combination thereof). In some cases, the processor 530 may be configured to operate a memory array using a memory controller. In other cases, a memory controller may be integrated into the processor 530. The processor 530 may be configured to execute computer-readable instructions stored in a memory 525 to perform various functions (e.g., functions or tasks supporting automated medication disposal messaging system).

Figure 6:
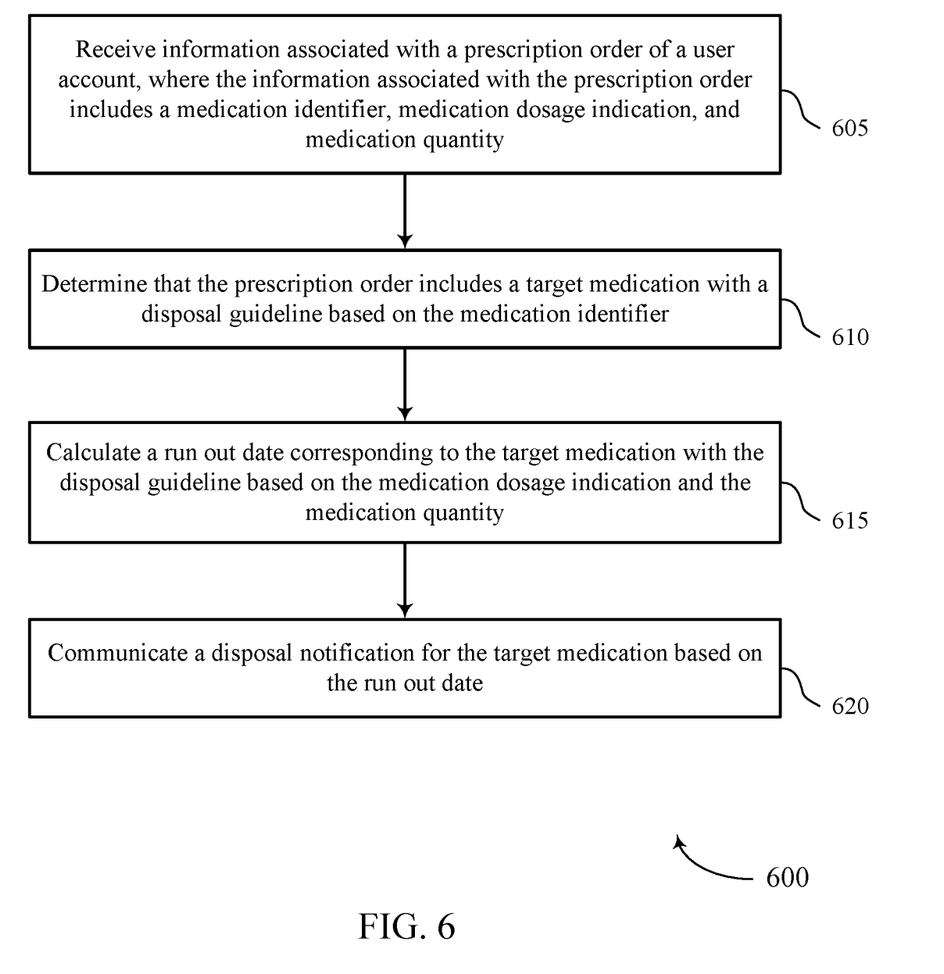
FIG. 6 shows a flowchart illustrating methods that support automated medication disposal messaging system in accordance with aspects of the present disclosure.

FIG. 6 shows a flowchart illustrating a method 600 that supports automated medication disposal messaging system in accordance with aspects of the present disclosure. The operations of method 600 may be implemented by a database server or its components as described herein. For example, the operations of method 600 may be performed by a medication disposal messaging manager as described with reference to FIGS. 3 through 5. In some examples, a database server may execute a set of instructions to control the functional elements of the database server to perform the functions described below. Additionally or alternatively, a database server may perform aspects of the functions described below using special-purpose hardware.

At 605, the database server may receive information associated with a prescription order of a user account, where the information associated with the prescription order includes a medication identifier, medication dosage indication, and medication quantity. The operations of 605 may be performed according to the methods described herein. In some examples, aspects of the operations of 605 may be performed by a pharmacy system interface component as described with reference to FIGS. 3 through 5.

At 610, the database server may determine that the prescription order includes a target medication with a disposal guideline based on the medication identifier. The operations of 610 may be performed according to the methods described herein. In some examples, aspects of the operations of 610 may be performed by a medication identification component as described with reference to FIGS. 3 through 5.

At 615, the database server may calculate a run out date corresponding to the target medication with the disposal guideline based on the medication dosage indication and the medication quantity. The operations of 615 may be performed according to the methods described herein. In some examples, aspects of the operations of 615 may be performed by a run out calculation component as described with reference to FIGS. 3 through 5.

At 620, the database server may communicate a disposal notification for the target medication based on the run out date. The operations of 620 may be performed according to the methods described herein. In some examples, aspects of the operations of 620 may be performed by a disposal messaging component as described with reference to FIGS. 3 through 5.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable read only memory (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for medication disposal messaging, comprising:
   receiving information associated with a prescription order of a user account, wherein the information associated with the prescription order comprises a medication identifier, medication dosage indication, and medication quantity;
   determining that the prescription order includes a target medication with a disposal guideline based at least in part on the medication identifier;
   calculating a run out date corresponding to the target medication with the disposal guideline based at least in part on the medication dosage indication and the medication quantity; and
   communicating a disposal notification for the target medication based at least in part on the run out date.

2. The method of claim 1, wherein the medication identifier comprises at least one of a drug name, a generic code number, a national drug code, or a generic product identifier.

3. The method of claim 1, wherein the medication dosage indication comprises at least one of a daily medication dosage or a total days' supply dispensed, and wherein the medication quantity comprises a total quantity of medication dispensed.

4. The method of claim 1, wherein the information associated with the prescription comprises information for providing contact associated with the user account.

5. The method of claim 4, wherein the information for providing contact associated with the user account comprises at least one of a primary contact number or a patient identifier.

6. The method of claim 1, wherein the target medication is designated as a controlled substance.

7. The method of claim 1, wherein the target medication is designated as a medication with disposal recommendations issued by a government agency.

8. The method of claim 1, wherein the disposal notification for the target medication comprises disposal instructions for any remaining target medication associated with the prescription order.

9. The method of claim 8, wherein the disposal instructions comprise instructions to utilize a neutralizing compound on any remaining target medication associated with the prescription order.

10. The method of claim 8, wherein the disposal instructions comprise instructions to return any remaining medication associated with the prescription order to a designated location.

11. The method of claim 1, further comprising:
    identifying a text-capable contact number associated with the information associated with the prescription order, and
    wherein the communicating comprises transmitting a message via the text-capable contact number to communicate the disposal notification for the target medication based at least in part on the run out date.

12. The method of claim 1, further comprising:
    identifying that a device associated with the user account comprises an application, and
    wherein the communicating comprises transmitting a push notification via the device to communicate the disposal notification for the target medication based at least in part on the run out date.

13. The method of claim 1, further comprising:
    identifying a contact number associated with the information for providing contact associated with the user account; and
    wherein the communicating comprises placing an outbound call to the contact number and providing an automated message to communicate the disposal notification for the target medication based at least in part on the run out date.

14. The method of claim 1, further comprising:
    receiving an incoming call from an inbound number; and
    identifying the prescription order of the user account user based at least in part on the inbound number and the information associated with the prescription order, and wherein the communicating comprises providing an automated message to communicate the disposal notification for the target medication based at least in part on the run out date.

15. The method of claim 1, wherein the communicating comprises communicating the disposal notification for the target medication on the run out date.

16. The method of claim 1, wherein the communicating comprises communicating the disposal notification for the target medication on a date that is less than a determined number of days before or after the run out date.

17. The method of claim 1, further comprising
receiving a notification that all medication associated with the prescription order was consumed.

18. The method of claim 1, further comprising
receiving a notification that any remaining medication associated with the prescription order was disposed.

19. An apparatus for medication disposal messaging, comprising:
a processor,
memory coupled with the processor; and
instructions stored in the memory and executable by the processor to cause the apparatus to:
receive information associated with a prescription order of a user account, wherein the information associated with the prescription order comprises a medication identifier, medication dosage indication, and medication quantity;
determine that the prescription order includes a target medication with a disposal guideline based at least in part on the medication identifier;
calculate a run out date corresponding to the target medication with the disposal guideline based at least in part on the medication dosage indication and the medication quantity; and
communicate a disposal notification for the target medication based at least in part on the run out date.

20. A non-transitory computer-readable medium storing code for medication disposal messaging, the code comprising instructions executable by a processor to:
receive information associated with a prescription order of a user account, wherein the information associated with the prescription order comprises a medication identifier, medication dosage indication, and medication quantity;
determine that the prescription order includes a target medication with a disposal guideline based at least in part on the medication identifier;
calculate a run out date corresponding to the target medication with the disposal guideline based at least in part on the medication dosage indication and the medication quantity; and
communicate a disposal notification for the target medication based at least in part on the run out date.

* * * * *